(12) United States Patent
Zand

(10) Patent No.: US 7,306,769 B2
(45) Date of Patent: Dec. 11, 2007

(54) BURNING APPARATUS

(76) Inventor: Farnaz Zand, 212 E. Providencia, Burbank, CA (US) 91502

( * ) Notice: Subject to any disclaimer, the term of this patent is extended or adjusted under 35 U.S.C. 154(b) by 368 days.

(21) Appl. No.: 10/964,248

(22) Filed: Oct. 12, 2004

(65) Prior Publication Data

US 2006/0078478 A1   Apr. 13, 2006

(51) Int. Cl.
*A61L 9/03* (2006.01)
(52) U.S. Cl. .............. 422/125; 431/288; 431/291; 431/335; 422/126
(58) Field of Classification Search ........... 422/307, 422/125, 126; 431/288, 291, 335
See application file for complete search history.

(56) References Cited

U.S. PATENT DOCUMENTS 5,094,223 A * 3/1992 Gonzalez .............. 126/25 R 6,190,439 B1 * 2/2001 Bresnahan et al. ........... 95/273

FOREIGN PATENT DOCUMENTS

JP  2001-327588 A  *  5/2000
JP  2002-102054 A  *  4/2002

OTHER PUBLICATIONS

Machine translation for JP 2002-102054A, http://www19.ipdl.ncipi.go.jp/PA1/cgi-bin/PA1INIT?1112640183462.*
Machine translation for JP 2001-327588A, http://www19.ipdl.ncipi.go.jp/PA1/cgi-bin/PA1INIT?1112640183462.*

* cited by examiner

*Primary Examiner*—Gladys J P Corcoran
*Assistant Examiner*—Sean E Conley
(74) *Attorney, Agent, or Firm*—James E. Brunton, Esq.

(57) ABSTRACT

A small, portable tabletop type burning apparatus for burning an aroma producing combustible material in a manner to produce soothing plumes of smoke for inhalation by the user.

5 Claims, 2 Drawing Sheets the
BURNING APPARATUS

BACKGROUND OF THE INVENTION

1. Field of the Invention

The present invention relates generally to small, portable tabletop devices for burning combustible materials. More particularly, the invention concerns a compact burning apparatus for burning an aroma producing combustible material in a manner to produce soothing plumes of smoke for inhalation by the user.

2. Discussion of the Prior Art

For hundreds of years, various cultures have controllably burned numerous types of combustible materials, such as certain seeds and crystalline materials, to produce soothing aromas that relieve stress and anxiety. By way of example, Persian cultures have for centuries controllably burned espand seeds and condor crystals in various manners, such as by heating the materials with burning charcoal. As these materials slowly burn they will emit an aromatic smoke that has a pleasant and soothing fragrance.

SUMMARY OF THE INVENTION

It is an object of the present invention to provide a compact, easy to use, attractive apparatus for controllably burning aroma producing combustible materials. More particularly, it is an object of the invention to provide such an apparatus in which a candle is used as a source of heat to controllably burn the combustible materials while at the same time providing a pleasant candlelight environment.

Another object of the invention is to provide an apparatus of the aforementioned character in which the combustible material to be burned is contained within a generally cup-shaped, perforated component that is supported over the candle by an attractive support housing.

Another object of the invention is to provide an apparatus of the character described in the preceding paragraphs, which is of a simple elegant construction, which can be easily cleaned after each use.

Another object of the invention is to provide an easily portable, light weight, tabletop type burning device that is safe and reliable in operation.

Another object of the invention is to provide an apparatus as described in the preceding paragraphs, which can be inexpensively manufactured.

By way of brief summary, one form of the apparatus of the invention for burning an aroma producing, combustible material comprises a housing having a base; an upper supporting surface disposed within a generally horizontal plane; and an internal chamber substantially open to atmosphere. A perforated, material supporting member is carried by the upper supporting surface of the housing for containing the combustible material, and a candle is disposed within the internal chamber for heating the combustible material to an elevated temperature sufficient to cause combustion of the material.

DESCRIPTION OF THE INVENTION

Figure 1:
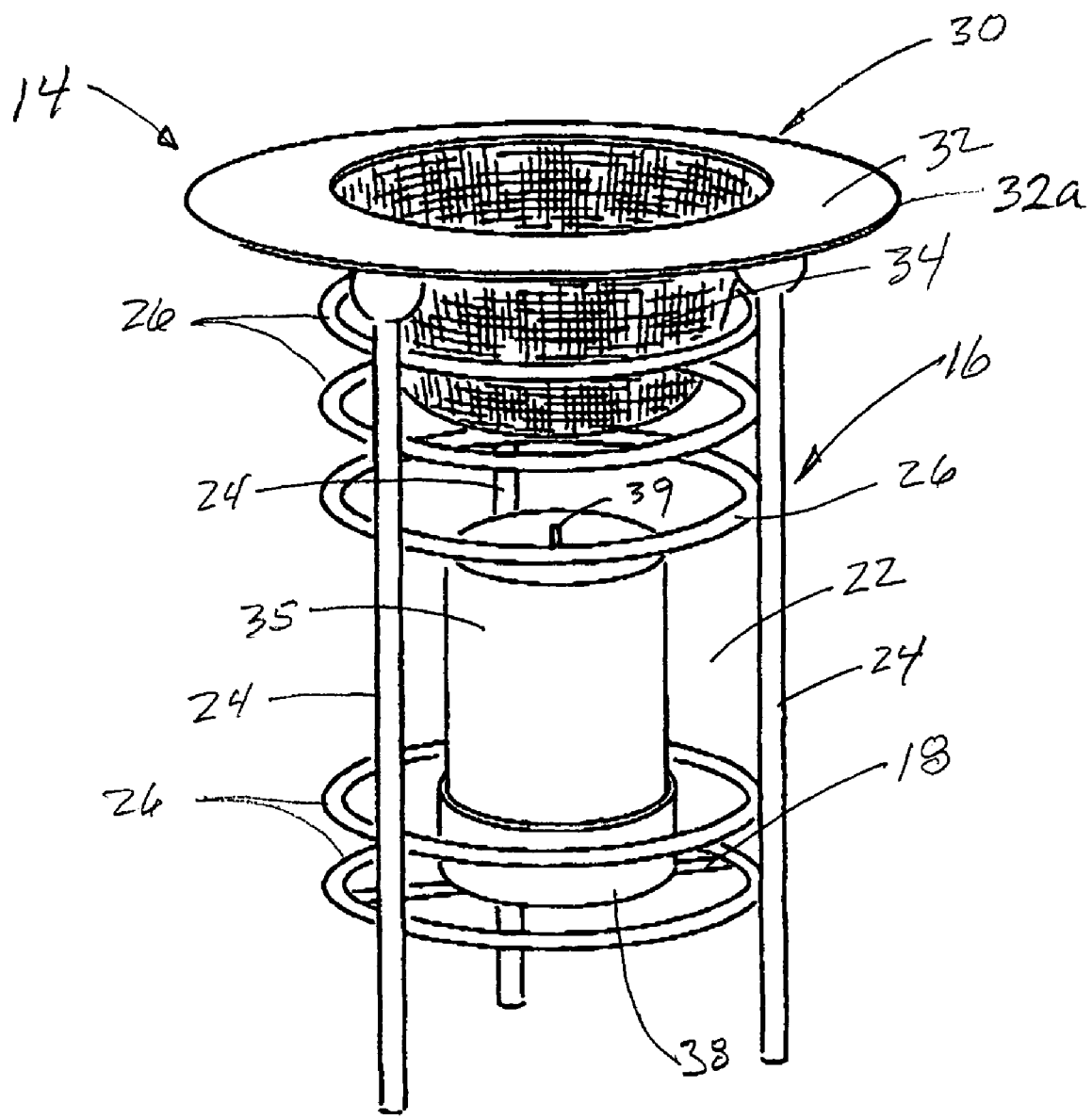
FIG. 1 is a generally perspective view of one form of the apparatus of the invention for burning aroma producing combustible materials.

Referring to the drawings, one form of the apparatus for burning an aroma producing, combustible material "M" is there shown and generally designated by 14. As previously mentioned, the material "M" (see FIG. 2) can comprise combustible seeds, such as "rose" espand, crystals, such as condor crystals, and a variety of other combustible materials, which, upon combustion, emit pleasant aromas.

Figure 2:
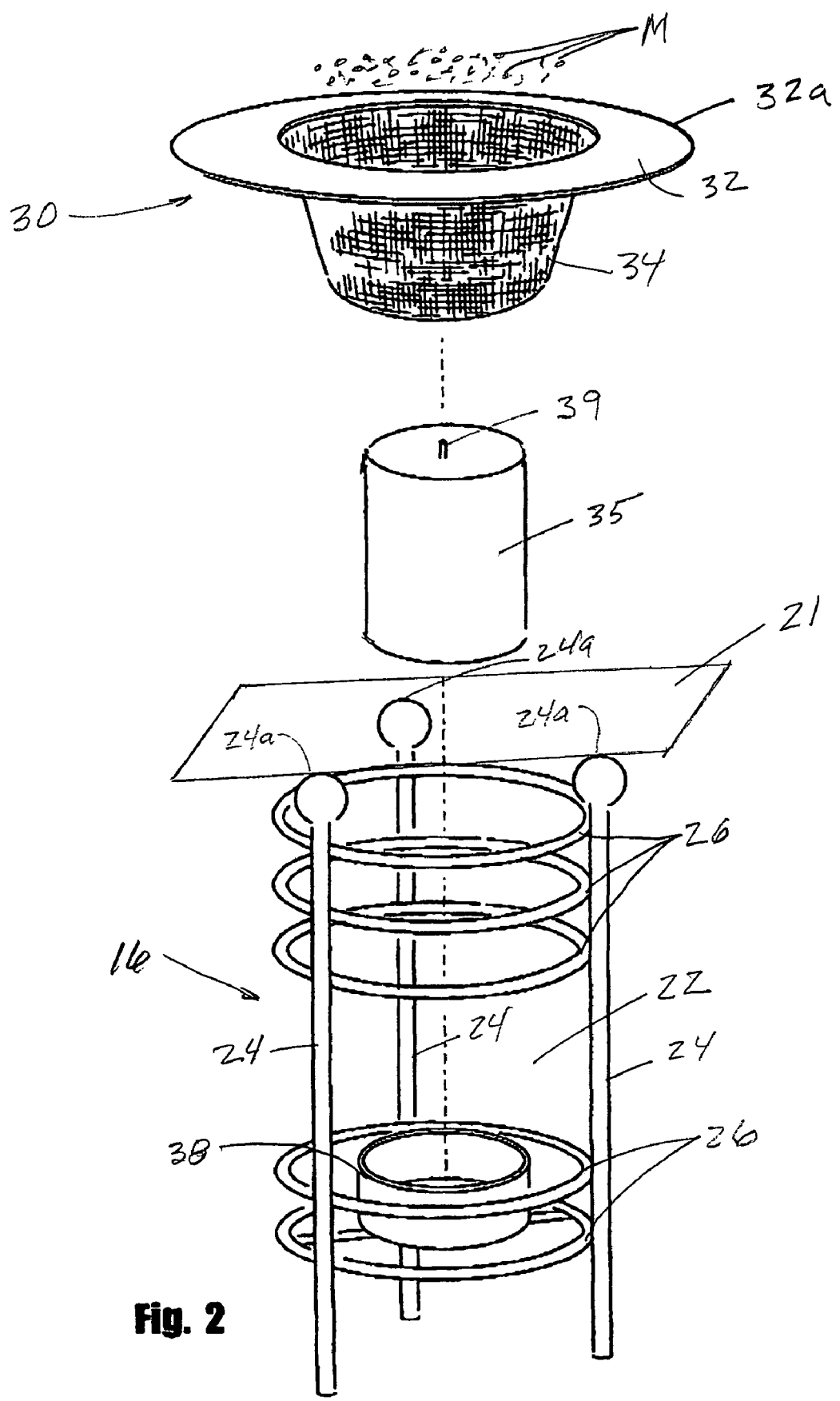
FIG. 2 is a generally perspective, exploded view of the form of the apparatus of the invention shown in FIG. 1.

In the present form of the invention the apparatus comprises a housing 16 having a base 18, an upper supporting surface that is disposed within a substantially horizontal plane 21 and an internal chamber 22 that is substantially open to atmosphere (FIG. 2). As best seen in FIG. 2, housing 16 is formed by a plurality of circumferentially spaced supporting columns 24 and a plurality of vertically spaced apart, generally ring-shaped chamber defining components 26 that are connected to the supporting columns 24 by any suitable means such as soldering or brazing. As indicated in FIG. 2, upper extremities 24a of supporting columns 24 reside within the plane 21. Columns 24 and rings 26 can be constructed from various materials, including metals and numerous fire resistant composite materials of a character well known to those skilled in the art.

Carried by upper extremities 24a of supporting columns 24 is a novel, material supporting assembly 30 for supporting the combustible material "M". Assembly 30 here comprises an upper, generally ring-shaped component 32 and a generally cup-shaped, perforated component 34 that is connected to and depends from ring-shaped component 32. Cup-shaped, perforated component 34 depends downwardly into internal chamber 22 and has the general configuration of a conventional, metal tea strainer. As indicated in the drawings, the periphery 32a of component 32 extends radially outwardly from the supporting columns 24 so that the material supporting assembly 30 can be easily lifted from the housing 16 by grasping the periphery of the ring-shaped component.

Disposed within internal chamber 22 of housing 16 is a flame producing means, shown here as a candle 35, which can be used to heat the combustible material "M" that is contained within perforated component 34 to an elevated temperature sufficient to cause the slow combustion of the material. As best seen in FIG. 2, a candle positioning means, shown here as a generally ring-shaped positioning component 38, is carried centrally of base 18 of housing 16. Positioning component 38 is strategically located in order to position the wick 39 of candle 35 in close proximity with the bottom of perforated component 34 in the manner illustrated in FIG. 1. Positioning component 38 can be constructed of several types of fire resistant materials, including various metals.

In using the apparatus of the invention, the combustible material "M" is first placed within the generally cup-shaped perforated component 34. With a candle 35 positioned within positioning component 38, the material supporting assembly 30 is mated with housing 16 so that the upper extremities 24a of the supporting columns 24 engage and support the lower surface of the ring-shaped component 32 of the material supporting assembly. With the components assembled in the manner shown in FIG. 1, the candle 35 can be lit to commence the heating of the material "M" contained within the perforated component 32. As the material is heated by the candle it will slowly burn and emit plumes of aromatic smoke for a soothing inhalation by the user.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for burning an aroma producing, combustible material comprising:
   (a) a housing having a base, an upper supporting surface and an internal chamber substantially open to atmosphere, said housing comprising a plurality of circumferentially spaced supporting columns and a plurality of vertically spaced-apart, generally ring-shaped chamber defining components connected to said plurality of circumferentially spaced supporting columns;
   (b) a material supporting member carried by said upper supporting surface of said housing for containing the combustible material, said material supporting member comprising a generally ring-shaped component and a generally cup-shaped, perforated component that is connected to and depends from said generally ring-shaped component into said internal chamber;
   (c) a candle disposed within said internal chamber for heating the combustible material to an elevated temperature sufficient to cause combustion of the material and;
   (d) a candle positioning means carried by said base of said housing for positioning said candle in close proximity to said generally cup-shaped perforated component of said material supporting assembly.

2. An apparatus for burning an aroma producing, combustible seeds comprising:
   (a) a housing having a base, an upper supporting surface disposed within a generally horizontal plane and an internal chamber substantially open to atmosphere, said housing comprising a plurality of circumferentially spaced supporting columns, each having an upper extremity residing within said generally horizontal plane and a plurality of vertically spaced-apart, generally ring-shaped chamber defining components connected to said plurality of circumferentially spaced supporting columns;
   (b) a material supporting assembly carried by said upper extremities of said circumferentially spaced supporting columns for containing the combustible seeds, said material supporting assembly comprising a generally ring-shaped component and a generally cup-shaped, perforated component connected to and depending from said generally ring-shaped component;
   (c) a candle disposed within said internal chamber for heating the combustible material to an elevated temperature sufficient to cause combustion of the material, said candle having an ignitable wick; and
   (d) a candle positioning means carried by said base of said housing for positioning said ignitable wick of said candle in close proximity to said generally cup-shaped perforated component of said material supporting assembly.

3. The apparatus as defined in claim 2 in which said candle-positioning means comprises a generally cylindrically shaped component carried by said base of said housing.

4. The apparatus as defined in claim 2 in which said generally cup-shaped, perforated component has the general configuration of a conventional metal tea strainer.

5. The apparatus as defined in claim 2 in which said a generally ring-shaped component has a periphery, said periphery extending radially outwardly from said supporting columns, whereby said material supporting assembly can be lifted from said housing by grasping said periphery of said ring-shaped component.

* * * * *